(12) United States Patent
Avirovikj et al.

(10) Patent No.: US 11,839,406 B2
(45) Date of Patent: Dec. 12, 2023

(54) BIOSENSOR INSERTERS AND METHODS WITH REDUCED MEDICAL WASTE

(71) Applicant: Ascensia Diabetes Care Holdings AG, Basel (CH)

(72) Inventors: Dragan Avirovikj, Stamford, CT (US); Jon Taylor, Groton, MA (US); John Longan, Nashua, NH (US); Chris Labak, Brookline, NH (US)

(73) Assignee: Ascensia Diabetes Care Holdings AG, Basel (CH)

( * ) Notice: Subject to any disclaimer, the term of this patent is extended or adjusted under 35 U.S.C. 154(b) by 8 days.

(21) Appl. No.: 17/581,842

(22) Filed: Jan. 21, 2022

(65) Prior Publication Data
US 2022/0226017 A1 Jul. 21, 2022

Related U.S. Application Data

(60) Provisional application No. 63/140,190, filed on Jan. 21, 2021.

(51) Int. Cl.
*A61B 17/34* (2006.01)
*A61B 5/00* (2006.01)
*A61B 5/145* (2006.01)

(52) U.S. Cl.
CPC ...... *A61B 17/3468* (2013.01); *A61B 17/3496* (2013.01); *A61B 5/0015* (2013.01); *A61B 5/14532* (2013.01); *A61B 5/6848* (2013.01)

(58) Field of Classification Search
CPC ............ A61B 17/3468; A61B 17/3496; A61B 2560/063; A61B 5/6848; A61B 5/6849; A61M 2205/3303; A61M 2005/1585
See application file for complete search history.

(56) References Cited

U.S. PATENT DOCUMENTS

| | | | |
|---|---|---|---|
| 8,333,714 B2 | 12/2012 | Stafford | |
| 8,862,198 B2 | 10/2014 | Stafford | |
| 9,662,071 B2 | 5/2017 | Ohkoshi | |
| 9,980,670 B2 | 5/2018 | Funderburk et al. | |

(Continued)

FOREIGN PATENT DOCUMENTS

| | | |
|---|---|---|
| CN | 101268932 A | 9/2008 |
| CN | 100591265 C | 2/2010 |

(Continued)

OTHER PUBLICATIONS

PCT Patent Application PCT/EP2022/051313 Notification of Transmittal of the International Preliminary Report on Patentability dated Mar. 6, 2023.

(Continued)

*Primary Examiner* — Majid Jamialahmadi
(74) *Attorney, Agent, or Firm* — ERISE IP, P.A.

(57) ABSTRACT

A biosensor inserter is configured to insert a biosensor. The biosensor inserter includes a push member including a receiver, a contact member translatable relative to the push member, and a trocar holder having a sheath configured to receive a trocar assembly including a trocar therein. The trocar holder is configured to be insertable into, and removable from, the receiver. Thus, an amount of medical waste can be minimized by discarding only the removable trocar holder and trocar assembly after use. System and method embodiments are provided.

20 Claims, 9 Drawing Sheets

(56) References Cited

U.S. PATENT DOCUMENTS

| | | |
|---|---|---|
| 10,292,632 B2 | 5/2019 | Lee et al. |
| 2008/0027296 A1 | 1/2008 | Hadvary et al. |
| 2008/0097246 A1 | 4/2008 | Stafford et al. |
| 2008/0319414 A1 | 12/2008 | Yodfat et al. |
| 2009/0257911 A1 | 10/2009 | Thomas et al. |
| 2010/0198033 A1 | 8/2010 | Krulevitch et al. |
| 2011/0106126 A1 | 5/2011 | Love et al. |
| 2012/0157801 A1 | 6/2012 | Hoss et al. |
| 2012/0197098 A1 | 8/2012 | Donnay et al. |
| 2013/0150691 A1 | 6/2013 | Pace et al. |
| 2013/0267811 A1 | 10/2013 | Pryor et al. |
| 2014/0066730 A1 | 3/2014 | Roesicke et al. |
| 2015/0018639 A1 | 1/2015 | Stafford |
| 2016/0058344 A1 | 3/2016 | Peterson et al. |
| 2016/0058474 A1 | 3/2016 | Peterson et al. |
| 2017/0143243 A1 | 5/2017 | Deck |
| 2017/0202488 A1 | 7/2017 | Stafford |
| 2017/0245798 A1 | 8/2017 | Ohkoshi |
| 2018/0116570 A1 | 5/2018 | Simpson et al. |
| 2018/0116572 A1 | 5/2018 | Simpson et al. |
| 2018/0325433 A1 | 11/2018 | Prais et al. |
| 2018/0368774 A1 | 12/2018 | Gray et al. |
| 2019/0223768 A1 | 7/2019 | Muller et al. |
| 2020/0009745 A1 | 1/2020 | Grossard et al. |
| 2020/0100713 A1 | 4/2020 | Simpson et al. |
| 2020/0214633 A1 | 7/2020 | Antonio |
| 2021/0052301 A1 | 2/2021 | Gass et al. |
| 2021/0052302 A1 | 2/2021 | Erekovcanski et al. |
| 2022/0071528 A1 | 3/2022 | Avirovikj et al. |
| 2022/0117627 A1* | 4/2022 | Garai ............... A61B 17/3468 |

FOREIGN PATENT DOCUMENTS

| | | |
|---|---|---|
| CN | 102065908 A | 5/2011 |
| CN | 103826528 A | 5/2014 |
| EP | 2636372 A1 | 9/2013 |
| EP | 2826422 A1 | 2/2015 |
| EP | 3170453 A1 | 5/2017 |
| EP | 3449827 A1 | 3/2019 |
| EP | 3449827 B1 | 5/2020 |
| JP | 2008508971 A | 3/2008 |
| JP | 2008246204 A | 10/2008 |
| JP | 2015509011 A | 3/2015 |
| WO | WO2013090215 A2 | 6/2013 |
| WO | WO2016036924 A2 | 3/2016 |
| WO | WO2018027940 A1 | 2/2018 |
| WO | 2018195286 A1 | 10/2018 |
| WO | WO2018195286 A1 | 10/2018 |
| WO | WO2018206552 A1 | 11/2018 |
| WO | WO2019054113 A1 | 3/2019 |
| WO | WO2019176324 A1 | 9/2019 |

OTHER PUBLICATIONS

U.S. Appl. No. 17/581,844, filed Jan. 21, 2022, Avirovikj et al.
International Search Report and Written Opinion of International Application No. PCT/EP2022/051313 dated May 11, 2022.

* cited by examiner

BIOSENSOR INSERTERS AND METHODS WITH REDUCED MEDICAL WASTE

CROSS REFERENCE TO RELATED APPLICATION

This application claims the benefit of U.S. Provisional Patent Application No. 63/140,190, filed Jan. 21, 2021, the disclosure of which is hereby incorporated by reference herein in its entirety for all purposes.

FIELD

The present disclosure relates to a biosensor inserter configured to insert a biosensor, which can be part of continuous analyte monitoring.

BACKGROUND

Continuous glucose monitoring, such as with a continuous glucose monitor (CGM) has become a routine sensing operation, particularly for sensing in diabetes care. By providing real-time glucose monitoring that provides glucose concentrations over time, therapeutic actions, such as insulin introduction, may be applied in a timely manner and the glycemic condition may be better controlled.

During a CGM operation, a biosensor of a transmitter and sensor assembly is inserted subcutaneously and is continuously operated in an environment surrounded by tissue and interstitial fluid (ISF). The biosensor is inserted under the skin and provides a signal to a transmitter of the transmitter and sensor assembly, and that signal can be indicative of a patient's blood glucose level, for example. These sensor measurements may be made intermittently and automatically many times throughout the day (e.g., every few minutes or other suitable interval).

The transmitter of the transmitter and sensor assembly is adhered to the outer surface of a user's skin, such as on the abdomen, on the back of the upper arm, or at another suitable location, while the biosensor is inserted through the skin so as to contact ISF. This skin insertion process may be referred to as "insertion." Devices for carrying out this biosensor insertion may be referred to as "biosensor inserters."

Biosensor inserter designs may be complicated and costly to manufacture. Moreover, some biosensor inserters are discarded as medical waste following their use.

SUMMARY

In some embodiments, a biosensor inserter configured to insert a biosensor is provided. The biosensor inserter includes a push member including a receiver, a contact member translatable relative to the push member, and a trocar holder configured to receive a trocar assembly including a trocar therein, the trocar holder is configured to be insertable into and removable from the receiver.

In further embodiments, a biosensor inserter is provided. The biosensor inserter includes a push member having a push element and a receiver; a trocar holder including a sheath portion, wherein the trocar holder is received in the receiver; a contact member configured to telescope relative to the push member; a transmitter carrier configured to support a transmitter and sensor assembly during insertion of the biosensor; a pivot member configured to pivot on the transmitter carrier; and a trocar assembly supported by the pivot member during insertion and retraction, the trocar assembly receivable in the sheath portion upon retraction.

In yet further embodiments, a method of using a biosensor inserter to insert a biosensor into a user is provided. The method includes providing the biosensor inserter comprising: a push member including a receiver, a trocar holder inserted in the receiver, the trocar holder including a sheath portion, a contact member translatable relative to the push member, and a trocar assembly including a trocar having a biosensor therein; contacting the contact member to skin of the user; pushing on the push member to cause insertion of the trocar and biosensor into the skin; continuing to push the push member to retract the trocar assembly into the sheath portion, while leaving the biosensor implanted; and removing the trocar holder and trocar assembly from the receiver.

Other features, aspects, and advantages of embodiments in accordance with the present disclosure will become more fully apparent from the following detailed description, the claims, and the accompanying drawings by illustrating a number of example embodiments. Various embodiments in accordance with the present disclosure may also be capable of other and different applications, and its several details may be modified in various respects, all without departing from the scope of the claims and their equivalents. Thus, the description is to be regarded as illustrative in nature, and not as restrictive.

BRIEF DESCRIPTION OF THE DRAWINGS

The drawings are to be regarded as illustrative in nature, and not as restrictive. The drawings are not necessarily drawn to scale. Like numerals are used throughout the drawings to denote like elements.

DETAILED DESCRIPTION

Figure 1:
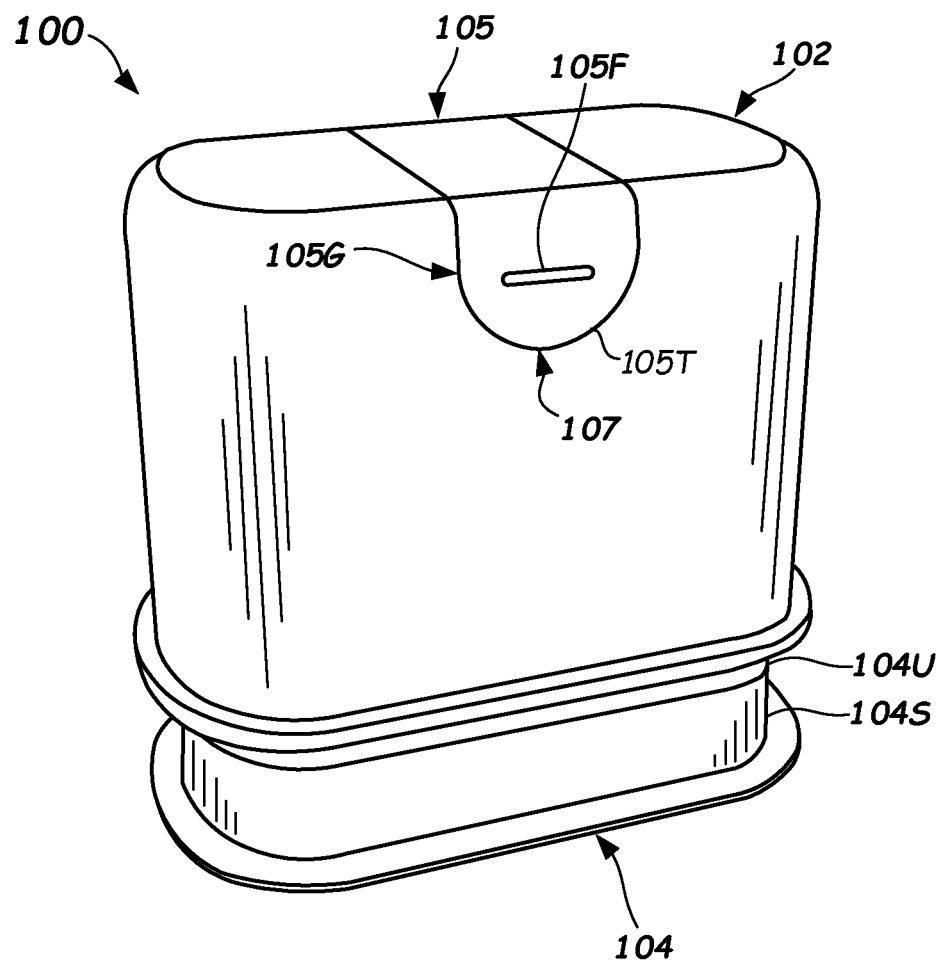
FIG. 1 is a side-perspective view of a biosensor inserter including a removable trocar holder in accordance with one or more embodiments provided herein.

A biosensor inserter is configured to implant (insert) a biosensor of a transmitter and sensor assembly into the skin of a person. In conventional biosensor inserters, a trocar assembly is used as part of the biosensor inserter wherein the trocar thereof aids in the insertion of the biosensor into the person. Once the biosensor insertion process is performed, the trocar assembly and trocar is retracted and generally remains inside of the biosensor inserter. Because blood may contaminate the trocar and biosensor inserter, conventional biosensor inserters are treated as a biohazard and are disposed of as medical waste, much like sharps.

Embodiments of the present disclosure operate to reduce the amount of medical waste generated by these biosensor inserters upon being used. This is accomplished by isolating the trocar assembly and trocar from the remaining part of the biosensor inserter. In one or more embodiments described herein, a biosensor inserter is provided that has parts thereof that are designed to be recycled, while other components are removable and are treatable as medical waste. Thus, the amount of medical waste is dramatically reduced, and the amount of recyclable material is increased. In accordance with some embodiments of the disclosure, after performing the insertion process with the biosensor inserter, a trocar holder carrying the trocar assembly is separated from the recyclable components by having the trocar assembly and trocar enclosed in a sheath portion of the removable trocar holder. Thus, after removal, the trocar holder and trocar contained therein can be discarded as medical waste. The remaining portions of the biosensor inserter can be recycled.

For example, in some embodiments, the biosensor inserter may include a push member configured to be pushed by a user (the person receiving the biosensor or another person), a contact member configured to contact the person's skin, and transmitter carrier that holds a transmitter and biosensor assembly during insertion of the biosensor. As the push member is pushed by the user, the transmitter carrier is translated toward a user's skin and the trocar and biosensor are inserted therein during a first portion of a stroke of the biosensor inserter. Continuing to push on the push member retracts the trocar, leaving the biosensor implanted in the user's skin.

In one or more embodiments, the push member includes a trocar holder that is registerable in a receiver of the push member and that is configured to contain the trocar assembly in a sheath portion after the insertion process is completed, wherein the trocar holder and trocar can be removed from the push member as a unit and discarded as medical waste. The push member, inner insertion/retraction mechanism, and contact member can be treated as recyclable material, since they would not be exposed to blood, nor would they contain any sharps. The largest volume of material is contained in the push member, inner insertion/retraction mechanism, and the contact member, thus only a small amount of material is considered medical waste, namely the trocar holder and trocar assembly. A trocar may also be referred to as an insertion portion.

In some embodiments, a skirt portion of the contact member, that is configured to be in contact with the person's skin, can be removable and can be removed and discarded as medical waste if it, has been contaminated by blood. Otherwise, it can be recycled.

FIGS. 1 through 3C illustrate various views of an embodiment of the biosensor inserter 100 including a push member 102 configured to be pushed by the user to cause insertion of the biosensor 314 (shown in FIG. 3B-3C) and a contact member 104 that is translatable (e.g., capable of telescoping) relative to the push member 102. Contact member 104 is configured to be in contact with the user's skin during biosensor insertion process. In the depicted embodiment, the push member 102 includes a receiver 107, which can be a pocket or other suitable opening. One type of mechanism 310 (FIG. 3A) of the biosensor inserter 100 is shown, which is operational to insert a trocar 212T of a trocar assembly 212 along with the biosensor 314 (FIGS. 3B-3C) and then retract the trocar assembly 212 and trocar 212T.

Further, biosensor inserter 100 includes a trocar holder 105 configured to hold the trocar assembly 212 after use so that it can be properly disposed of. The trocar holder 105 may provide a secondary function of providing a guide for the proper alignment of the trocar assembly 212 during insertion. For example, a body 312B (FIG. 3B) of the trocar assembly 212 may have a shape, such as rectangular cross-sectional shape shown, that is similar to, but slightly smaller than an internal shape of an internal channel (e.g., hollow interior 205I—FIG. 2) formed in the sheath portion 205S of the trocar holder 105 such that the body 312B of the trocar assembly 212 can slide in the hollow interior 205I, but not rotate or tilt therein. The trocar holder 105 is configured to be insertable into, and removable from, the receiver 107. Thus, the trocar holder 105 and trocar assembly 212 are removable (can be removed from) from the receiver 107 of the push member 102 and safely discarded as medical waste after use.

Figure 2:
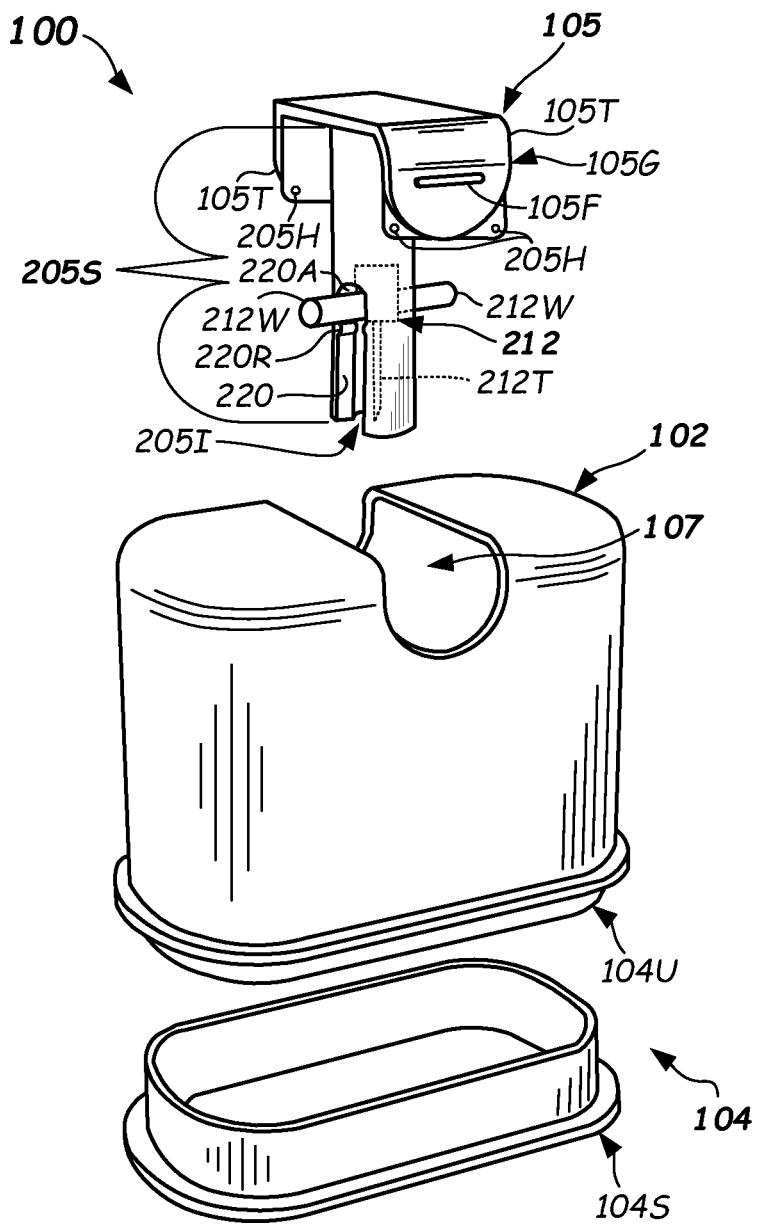
FIG. 2 is a partial exploded side view of a biosensor inserter including a removable trocar holder holding a trocar assembly in accordance with one or more embodiments provided herein.
Figure 3A:
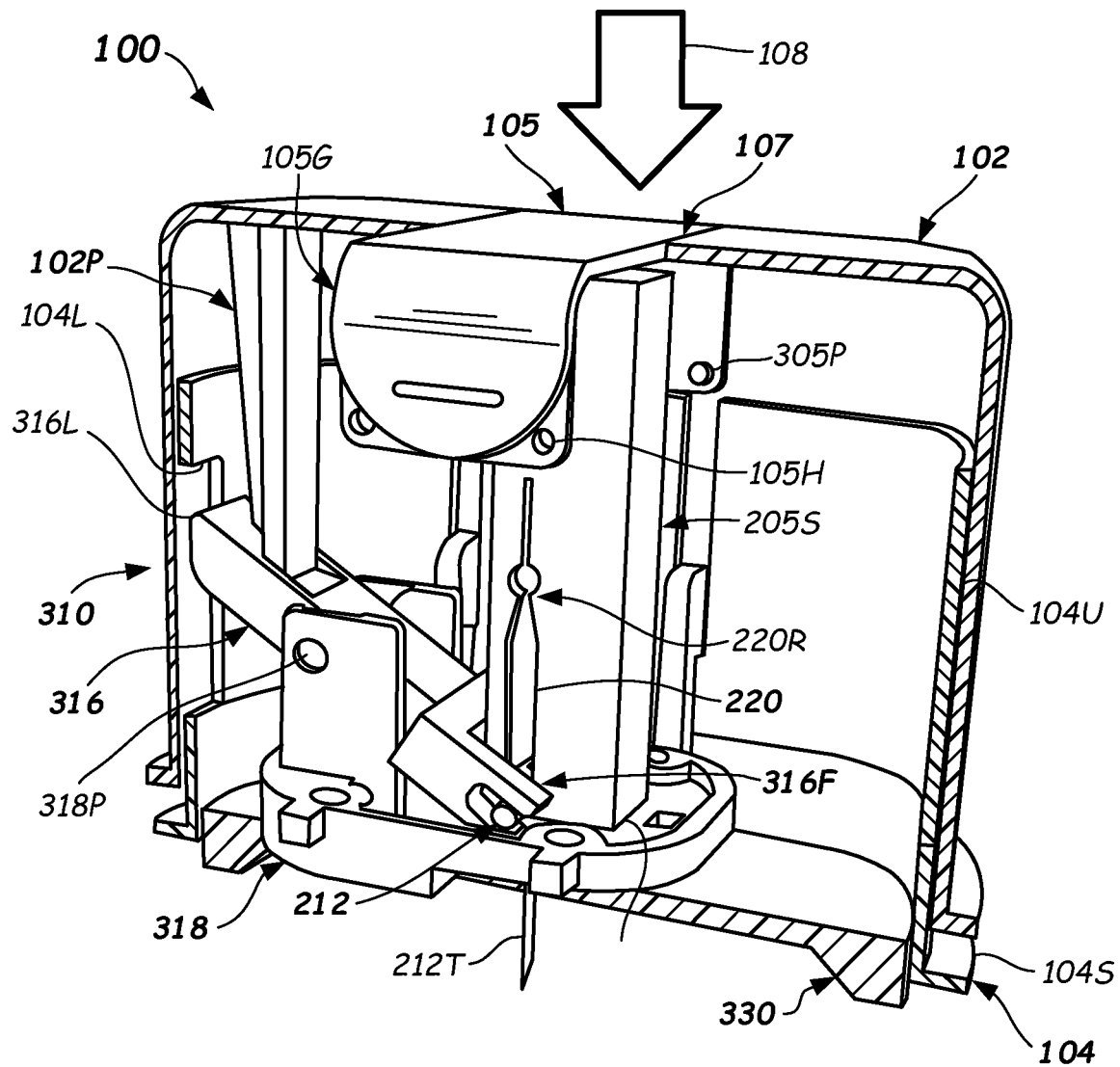
FIG. 3A is a cross-sectioned, perspective side view of a biosensor inserter illustrated in an extended configuration used when inserting the trocar and biosensor in accordance with one or more embodiments provided herein.
Figure 3B:
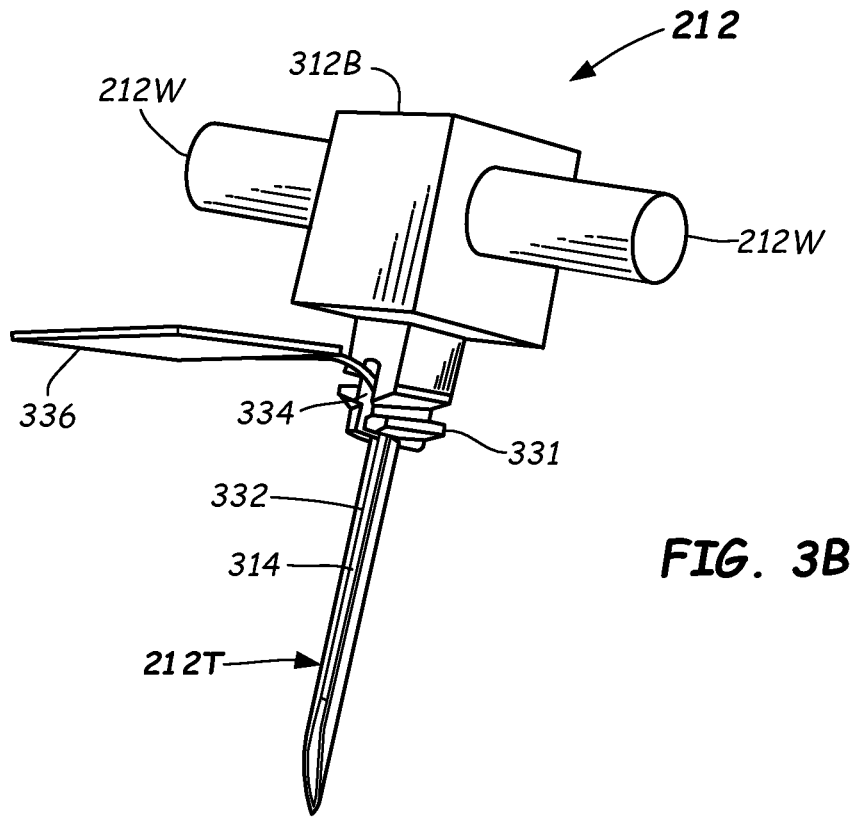
FIG. 3B is a perspective side view of a trocar assembly including a trocar and a biosensor in accordance with one or more embodiments provided herein.
Figure 3C:
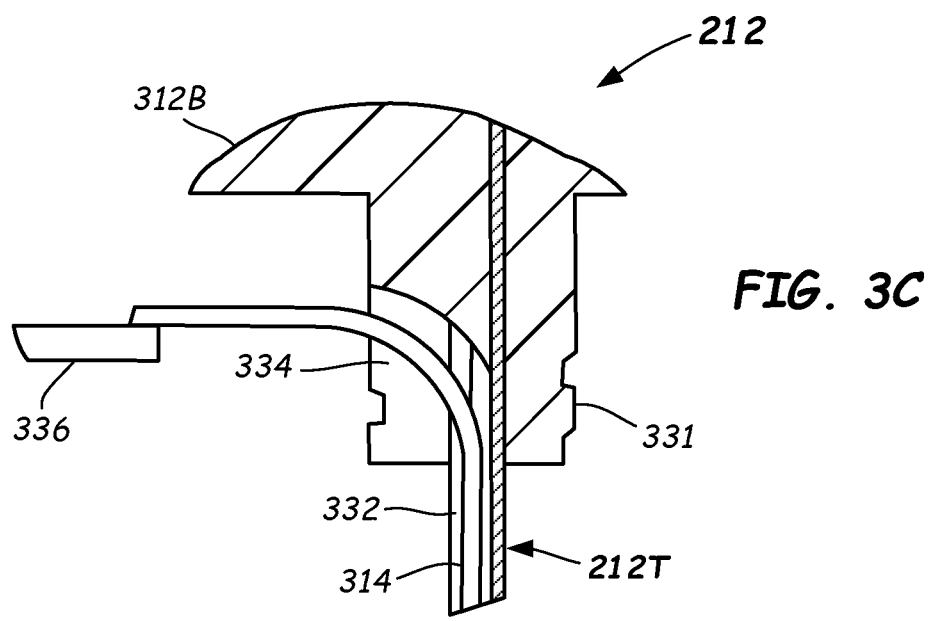
FIG. 3C is an enlarged, cross-sectioned, partial side view of a trocar assembly illustrating the biosensor transitioning into a side groove of the trocar in accordance with one or more embodiments provided herein.

Again referring to the trocar assemblies 212 shown in FIGS. 2 and 3B and 3C, the body 312B of the trocar assembly 212 can include wings 212W extending laterally therefrom. The wings 212W ride in the slots 220 formed in sides of the sheath portion 205S of the trocar holder and can snap past one or more retention features 220R upon retraction of the trocar assembly 212. Thus, the slots 220 formed in sides of the sheath portion 205S are configured to receive wings 212W of the trocar assembly 212. The one or more retention features 220R can be configured to secure the trocar assembly 212 to the sheath portion 205S. Further, the one or more retention features 220R can comprise a narrowed portion of a slot 220 formed in one or more sides of the sheath portion 205S that are configured to receive wings 212W of the trocar assembly 212. As shown in FIG. 3A, forks 316F of the pivot member 316 engage the wings 212W of the trocar assembly 212 to drive same and cause biosensor insertion and thereafter retraction. In particular, the pivot member 316 comprises a forked end including forks 316F with a first fork and a second fork that can straddle the sheath portion 205S of the trocar holder 105, wherein each fork 316F can include an open-ended groove configured to receive the wings 212W therein.

Receiver 107 may be a pocket formed in a top portion of the push member 102 in some embodiments. For example, as shown in FIG. 2, the receiver 107 can be formed in a top and/or side(s) of the push member 102. As shown, the grasping portion 105G of the trocar holder 105 is configured to be grasped by a thumb and finger of the user. Any suitable surface feature 105F or features that enhance gripping of the trocar holder 105 can be added to the side surfaces of the grasping portion 105G, such as by adding a raised portion (e.g., raised rib) as shown. Optionally one or more indented portions or other grip feature may be provided to enhance gripping. Additionally, as shown in FIGS. 2 and 3A, retention features may be added to the trocar holder 105, such as to grasping portion 105G. Retention features in this embodiment can comprise holes 205H formed in tabs of the sides of the gripping portion 105G as shown. The holes 205H can register with pilots 305P (FIG. 3A) formed on the body portion of the push member 102.

Figure 5:
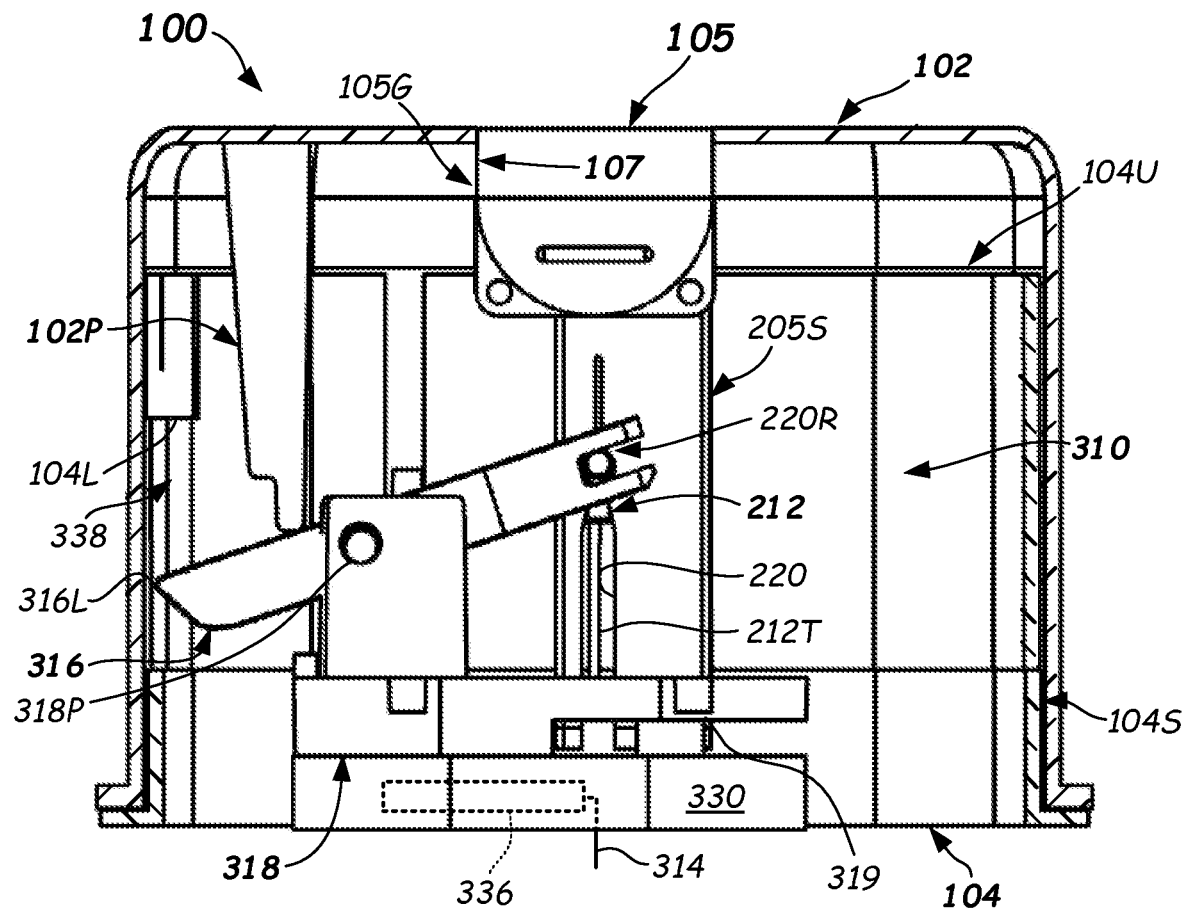
FIG. 5 is a cross-sectioned side view of a biosensor inserter illustrated in a retracted position with the trocar assembly coupled to the removable trocar holder in accordance with one or more embodiments provided herein.

FIG. 2 further illustrates the sheath portion 205S of the trocar holder 105 in more detail. Trocar holder 105 includes the sheath portion 205S extending from the grasping portion 105G. Sheath portion 205S includes a hollow interior 205I that can receive a portion of the trocar assembly 212 therein. After the insertion of the biosensor 314, the trocar assembly 212 is retractable by pivot member 316 into the hollow interior 205I of the sheath portion 205S, similar to what is shown in FIGS. 2 and FIG. 5.

As shown, the sharp end of the trocar 212T can be retracted so that it is located fully inside of the hollow interior 205I so that the sharp end is sheathed and this contact therewith is minimized. This is achieved by the pivoting of the pivot member 316 as shown in FIG. 5, which moves the wings 212W of the trocar assembly 212 up in the slots 220 past the retention features 220R and effectively locks the wings 212W into the retention area 220A (See FIG. 2) of the trocar assembly 212 where the wings 212W are held securely so that the trocar assembly 212 cannot fall out of the sheath portion 205S.

As the trocar assembly 212 is captured within the hollow interior 205I, the user can squeeze the opposing side tabs 105T of the grasping portion 105G sufficiently to move the holes 205H past the pilots 305P and thus remove the trocar holder 105 along with the trocar assembly 212. Thus, the material considered medical waste can be isolated away from the remaining recyclable portion. The trocar holder 105 along with the trocar assembly 212 can then be disposed as medical waste. Similarly, in a separate step, the skirt 104S can also be removed and disposed of as medical waste, if contaminated. Skirt 104S may be part of the contact member 104 and may slip over, or otherwise be removably fastened to, the upper portion 104U of the contact member 104.

FIGS. 3A and 4-7 illustrate the mechanism 310 of the biosensor inserter 100. In some embodiments, the pivot member 316, which contacts and operatively drives the trocar assembly 212, is restrained from pivoting as the transmitter carrier 318 translates toward a user's skin during a first portion (insertion portion) of the stroke of the biosensor inserter 100, but is allowed to pivot once delatched after the biosensor 314 is implanted in a user's skin. Once delatched, the pivot member 316 may pivot in a second portion of the stroke of the biosensor inserter 100, which causes the retraction (the retraction portion of the stroke) of the trocar assembly 212 and leaves the biosensor 314 inserted into the user's skin. Thus, the pivot member 316 does not pivot in the first portion of the stroke, and does pivot in a second (retraction) portion of the stroke. The transmitter carrier 318 is translatable relative to the contact member 104 and is configured to support a transmitter and sensor assembly 330 during insertion of a biosensor 314 (FIG. 3B). The transmitter carrier 318 may include an aperture 319 configured to receive the sheath portion 205S therein during insertion. Other suitable mechanisms for insertion and retraction may be used.

FIGS. 3A and 4-7 further illustrate cross-sectional side views of a biosensor inserter 100 shown in various portions of the stroke in accordance with one or more embodiments provided herein. The contact member 104 includes an upper portion 104U and a skirt 104S at the lower end. Lower end, which may be part of skirt 104S, may contact a user's skin during insertion and retraction of the trocar assembly 212 to implant a biosensor 314. Contact member 104 further includes a latch 104L, which has a latch surface (lower latch surface) that once passed by via motion of a latch end 316L of the pivot member 316 will allow the pivot member 116 to rotate (FIG. 5). The pivot member 316 can be configured to pivot on the transmitter carrier 318, such as about pivot 318P.

For example, pivot 318P may include laterally extending features (e.g., posts) formed on the pivot member 316 that interface with holes or recesses formed in first and second side supports of transmitter carrier 318 (see FIG. 3A) to form a pivot axis. Thus, the pivot member 316 is pivotable about the pivot axis and pivots on the pivot of 318P formed by transmitter carrier 318 and pivot member 316.

A pivot location of the pivot 318P can be formed between the latch end 316L and the opposite end of pivot member 316 containing the forks 316F. Other suitable laterally extending features may be used to form the pivot 318P, and other pivot mechanisms may be used, such as a removable axle, or the like.

Latch 104L may be formed as an opening in the sidewall of the contact member 104. The latch 104L can comprise a circumferentially disposed surface of a width that can be wider than the latch end 316L of the pivot member 316. Up until when the latch end 316L passes by the latch 104L, the pivot member 316 is restrained from rotation about pivot 318P. As shown, latch 104L is part of a vertically extending cutout that may be closed at its lower end by skirt 104S. Once past the latch 104L, the pivot member 316 may rotate.

As shown in FIGS. 3A-7, push member 102 may include a push element 102P, which can be a rigid member that extends downwardly (as oriented in FIG. 3A) from the underside of push member 102 and includes a contact end that engages with pivot member 316. Push element 102P engages with pivot member 316 and causes rotation (pivoting) thereof as well as translation of the transmitter carrier 318. Transmitter carrier 318 can be received within the contact member 104 and can have a transmitter and sensor assembly 330 coupled thereto. Transmitter and sensor assembly 330 includes the transmitter electronics and radio that can be used to communicate measured analyte values and/or other data received from the implanted biosensor 314 to a reader, smartphone executing a suitable application, or other apparatus for processing and displaying analyte values, including trends. Transmitter and sensor assembly 330 further includes a biosensor 314 coupled thereto, which has a reading end that is received inside of the trocar 212T and is inserted with the aid of the trocar 212T and after which the trocar 212T is removed and the biosensor 314 remains implanted in the person.

In operation, the transmitter and sensor assembly 330 can be detachably coupled to the transmitter carrier 318. Transmitter and sensor assembly 330 can include an adhesive layer to adhere the transmitter and sensor assembly 330 to the user's skin upon retraction of the trocar assembly 212. Any suitable mechanism that allows detachment of the transmitter and sensor assembly 330 from the transmitter carrier 318 may be used, such as a pressure sensitive adhesive, a slight interference fit, a low-release force retention mechanism, or the like.

In some embodiments, the push member 102, contact member 104, pivot member 316, and/or transmitter carrier 318 may be formed from a biodegradable and/or recyclable material (e.g., a recyclable plastic, a biodegradable paper product, bamboo, etc.). In particular, in some embodiments, recyclable plastics may be used for the above-listed components, including, but not limited to, polyethylene terephthalate (PET), high-density polyethylene (HDPE), low-density polyethylene (LDPE), polyvinyl chloride, polypropylene, polystyrene, and the like.

In more detail, the transmitter carrier 318 is axially translatable relative to the contact member 104 and is configured to support the transmitter and sensor assembly 330 during insertion of the biosensor 314. In particular, the transmitter and sensor assembly 330 may include transmitter electronics 336, a power source (not shown), and a biosensor assembly that includes the biosensor 314.

The transmitter and sensor assembly 330 may include transmitter electronics 336 (FIG. 3B) that may include an analog front end for biasing the biosensor 314 and for sensing current that passes through the biosensor 314, such as an operational amplifier or amplifiers, current sensing circuitry, processing circuitry such as an analog-to-digital converter for digitizing current signals, memory for storing digitized current signals, a controller such as a microprocessor, microcontroller or the like for possibly computing analyte concentration values based on measured current signals, and transmitter circuitry for transmitting analyte concentration values to the external device (e.g., a smart phone or another suitable external reader device configured to store and/or displaying analyte concentrations).

In some embodiments, the biosensor 314 used within the transmitter and sensor assembly 330 may include two electrodes and the bias voltage may be applied across the pair of electrodes. In such cases, current may be measured through the biosensor 314. In other embodiments, the biosensor 314 may include three electrodes such as a working electrode, a counter electrode, and a reference electrode. In such cases, the bias voltage may be applied between the working electrode and the reference electrode, and current may be measured through the working electrode, for example. The biosensor 314 may include an active region including one or more chemicals that undergo an analyte-enzyme reaction with the products they detect. The enzyme can be immobilized on one or more electrodes to provide a reaction (e.g., redox reaction) with the analyte and generate a current at the electrodes. Example chemicals include glucose oxidase, glucose dehydrogenase, or the like for measuring glucose as an analyte. In some embodiments, a mediator such as ferricyanide or ferrocene may be employed at the active region. In general, any analyte that may be detected and/or monitored with a suitable biosensor and for which suitable chemistry exists may be measured, such as glucose, cholesterol, lactate, uric acid, alcohol, or the like. An analyte is defined herein as a component, substance, chemical species, or chemical constituent that is measurable in an analytical procedure.

An example of the biosensor 314 can be any suitable implantable sensor that can be implanted in the skin of a user, such as a strand-shaped sensor shown in FIGS. 3B-3C that is able to be received inside of a side groove 332 formed lengthwise in the trocar 212T of the trocar assembly 212 and that is able to sense an analyte concentration of an interstitial fluid under the skin.

Trocar 212T of trocar assembly 212 may be made, for example, from a metal such as stainless steel, or a non-metal such as plastic. Other suitable materials may be used. In some embodiments, trocar 212T may be have a lengthwise formed side groove 332 formed from, but not limited to, a round C-channel tube, a round U-channel tube, a stamped sheet metal part folded into a U-profile in cross-section, a molded/cast metal part with a U-channel profile in cross-section, or a solid metal cylinder with an etched or ground channel causing a U-shapes cross-section. Other trocar shapes may be used that allow insertion and retraction, while leaving behind the implanted biosensor 314.

Body 312B of trocar assembly 212 may be formed from a suitable plastic, for example, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethylene (LDPE). Other suitably rigid materials may be used.

As best shown in FIGS. 3B and 3C, the biosensor 314 is received in the side groove 332 of the trocar 212T, that extends along the length of the trocar 212T, and transitions into a passage 334 formed in the threaded portion 331, and then passes laterally out of passage 334 to connect to the transmitter electronics 336 such as an electrical circuit board, or other like electronic component including, coupled to, or configured to couple to other electronics of the transmitter and sensor assembly 330. Thus, upon insertion and then retraction of the trocar 212T in and from the user's skin, the biosensor 314 can remain in place by being removed from passage 334 and the side groove 332.

In operation, the trocar assembly 212 can be drivable by being contacted by the forks 316F of the pivot member 316 in an insertion stroke to insert the biosensor 314 into the user's skin. In particular, trocar assembly 212 is drivable by the wings 212W of the body 312B being received in the open-ended grooves formed in the forks 316F of the pivot member 316. Further, the body 312B may include a rectangular portion that is received in a like rectangular portion of the hollow interior 205I. As discussed above, the rectangular portions may interface and provide an anti-rotation support.

As best shown in FIG. 3A, contact member 104 may be configured to be concentric with push member 102 and may be telescopic therewith. In some embodiments, contact member 104 may include a first alignment feature such as a vertically extending groove or recess, and transmitter carrier 318 may include a second alignment feature, such as a vertically extending finger tab, that interfaces with the first alignment feature. Such alignment features may hold contact member 104 and transmitter carrier 318 in rotational alignment to prevent rotation there between, such as during the insertion and retraction portions of the stroke. Push member 102 and contact member 104 may be oval or oblong as shown, or optionally circular, elliptical, or any other suitable shape in transverse cross-section. In some embodiments, push member 102 and contact member 104 may not be concentric.

Operation of the biosensor inserter 100 is now described with reference to FIGS. 4-7, which illustrate cross-sectional side views of the biosensor inserter 100 during various portions of the stroke of the insertion method operative to insert a biosensor 314 in accordance with embodiments provided herein. In addition, FIG. 8 illustrates a flowchart of a method 800 of using a biosensor inserter 100 to insert a biosensor 314 in accordance with embodiments provided herein.

Figure 8:
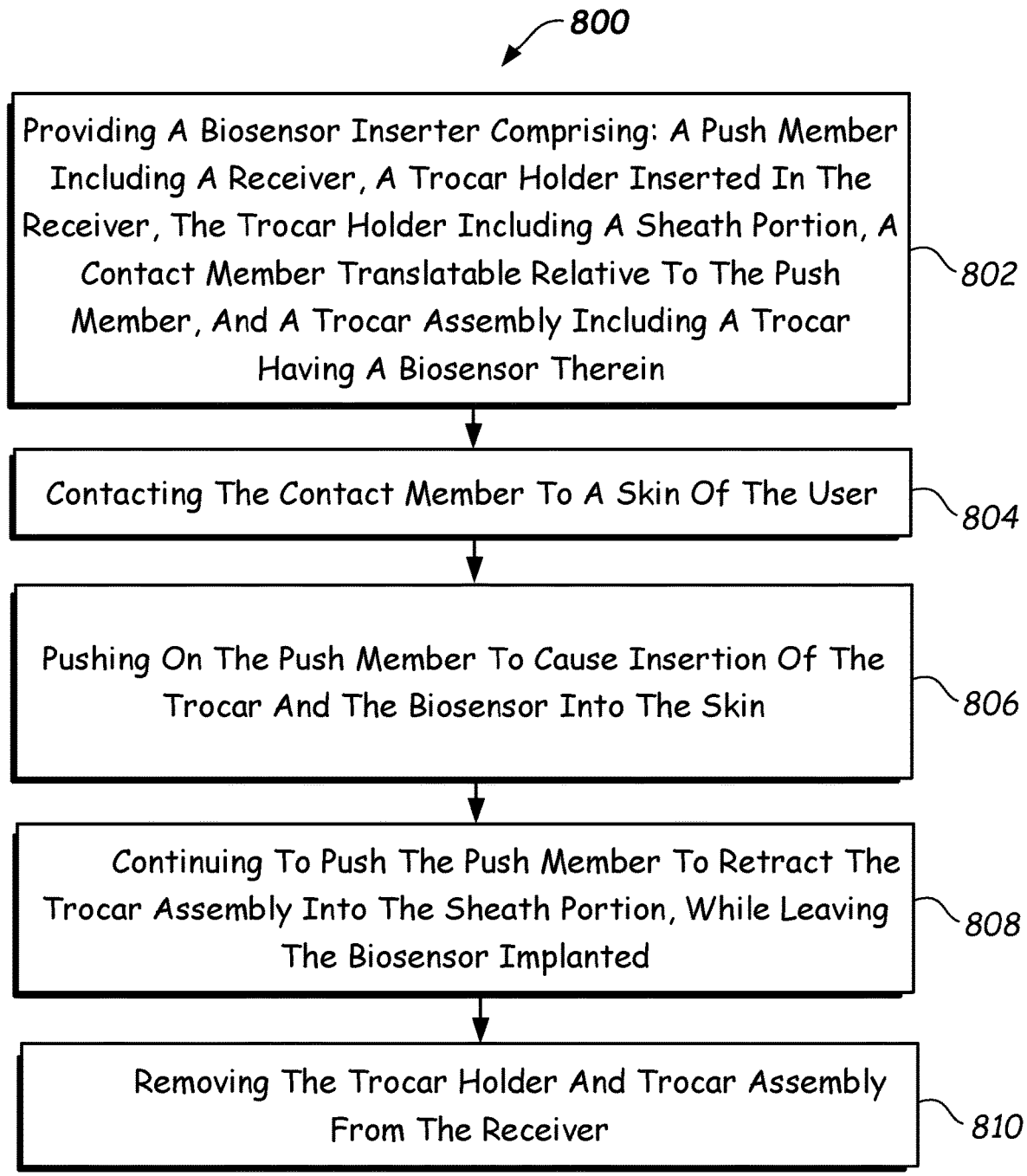
FIG. 8 illustrates a flowchart of a method of using a biosensor inserter to insert a biosensor in a user in accordance with embodiments provided herein.

To begin the insertion method 300 of FIG. 8, a needle cover (not shown) can be removed from threaded portion 331 of trocar assembly 212 of the biosensor inserter 100. The biosensor inserter 100 is placed in contact with the skin surrounding a desired insertion site of a user, such as on an upper arm, an abdomen region, or another suitable location.

To begin insertion, a force 108 is applied to the push member 102 by a user so as to cause the push member 102 to translate relative to the contact member 104 and move toward the insertion site. Movement of push member 102 over the contact member 104 causes push element 102P to contact the pivot member 316, which causes transmitter carrier 318 and pivot member 316 to translate and move toward the insertion site with the latch end 316L moving linearly relative toward the latch 104L along the wall.

During this first portion of the stroke of the method 800, pivot member 316 is prevented from pivoting via the contact of the latch end 316L with the wall of the contact member 104. Thus, transmitter carrier 318 and coupled transmitter and sensor assembly 330 translate toward the insertion site.

Figure 4:
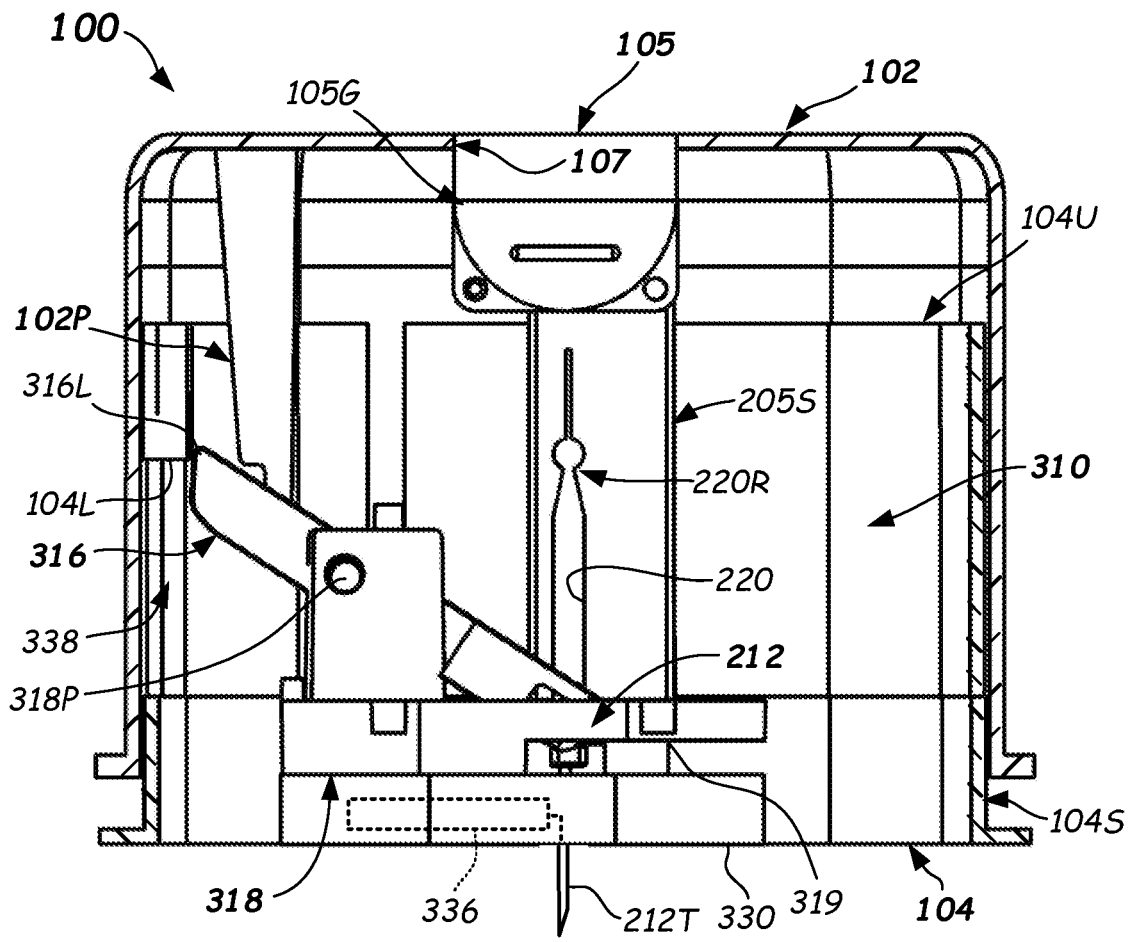
FIG. 4 is a cross-sectioned side view of a biosensor inserter illustrated in a first extended position where the trocar and biosensor would be inserted into the skin of the person in accordance with one or more embodiments provided herein.

As shown in FIG. 4, transmitter carrier 114 and transmitter and sensor assembly 330 continue to move toward the insertion site and trocar 212T makes contact and enters insertion site of the skin, and a bottom surface of transmitter and sensor assembly 330 contacts the skin around the insertion site. In some embodiments, bottom surface of transmitter and sensor assembly 330 may adhere (e.g., via an adhesive material) to the user's skin surrounding the insertion site. The trocar 212T and biosensor 314 enters the insertion site where biosensor 314 can make contact with interstitial fluid in the subcutaneous region. The biosensor 314 can be placed 4 mm to 6 mm into the skin, for example, although other depths may be used.

As shown in FIG. 5, following insertion of the biosensor 314 (including adhesion of the transmitter and sensor assembly 330 to the skin around the insertion site), the push member 102 continues to move relative to the contact member 104 in a second portion of the stroke. When the latch end 316L of the pivot member 316 moves past the latch 104L at the start of the second portion of the stroke, the pivot member 316 is allowed to pivot via the pushing by push element 102P, rotate under latch 104L about pivot 318P and into cutout portion 338. The pivoting causes the retraction of the trocar assembly 212 in the second portion of the stroke.

During the retraction, pivot member 316 pivots on the transmitter carrier 318 due to the force 108 applied by push element 102P on pivot member 316. As this occurs, trocar assembly 212 retracts from the insertion site and moves away from transmitter and sensor assembly 330, which is adhered to the user. As the push member 102 continues to move relative to the contact member 104 toward the insertion site, push element 102P continues to press against pivot member 316. Eventually, as shown in FIG. 5, pivot member 316 pivots sufficiently for trocar assembly 212 to be completely removed from the user's skin and leaves the implanted biosensor 314 therein. As the push member 102 is continued to be pushed further, the trocar assembly 212 is retracted along slots 220 and past retention feature 220R. Additionally, the trocar assembly 212 is retracted into the sheath portion 205S of the trocar holder 105 and securely held thereby.

Biosensor inserter 100 then may be removed, leaving transmitter and sensor assembly 330 in place, with the bottom surface of transmitter and sensor assembly 330 adhered to the user's skin at the insertion site and biosensor 314 in contact with interstitial fluid of the user.

Figure 6:
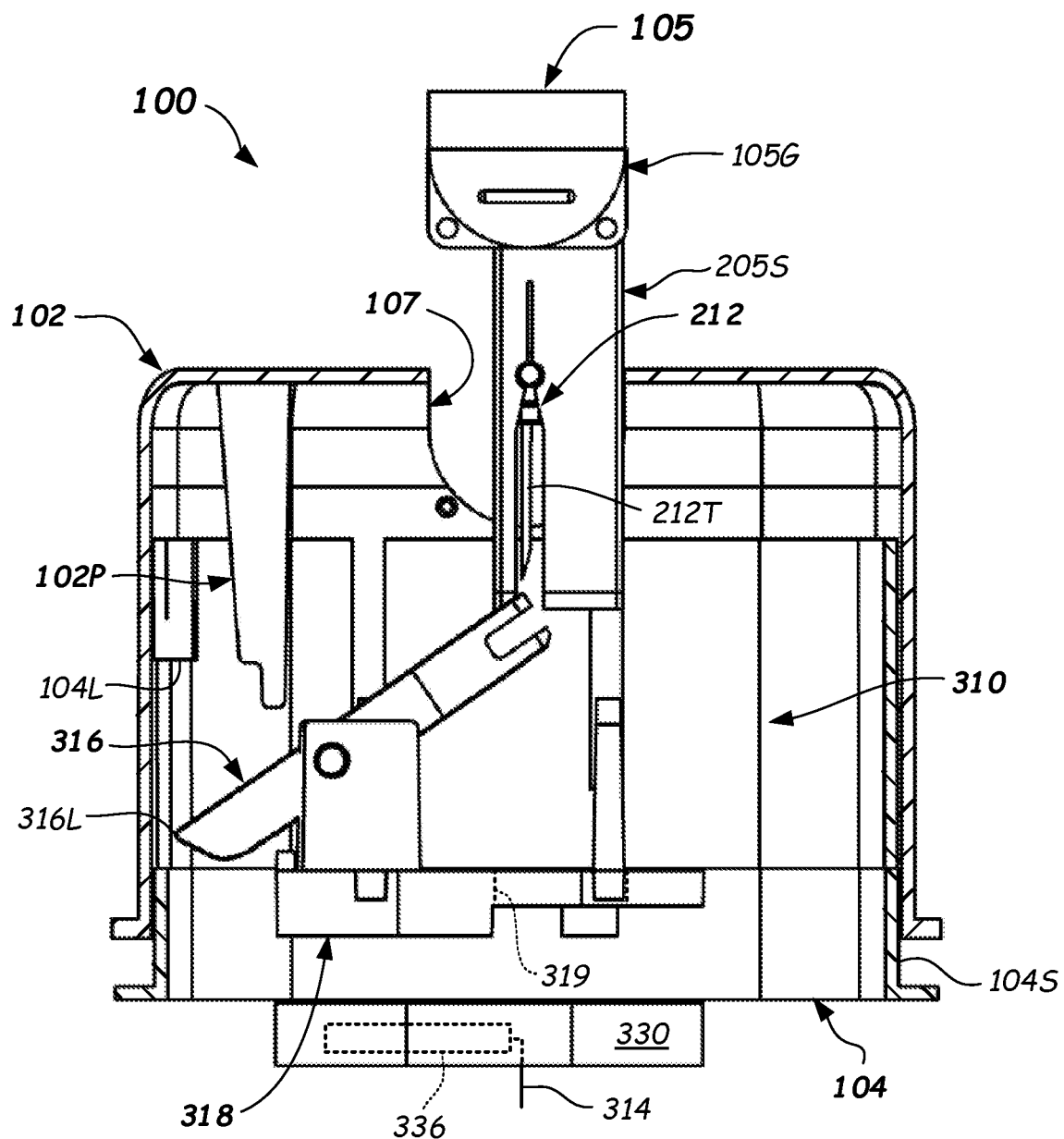
FIG. 6 is a cross-sectioned side view of a biosensor inserter illustrated with the trocar and trocar holder being removed from the remainder of the biosensor inserter in accordance with one or more embodiments provided herein.

Before or after removal of the biosensor inserter 100, the trocar holder 105 with the trocar assembly 212 contained and held therein can be removed, such as shown in FIG. 6. The trocar assembly 212 is secured in the trocar holder 105 and can be discarded therewith as medical waste.

In some embodiments, the push member 102, contact member 104, pivot member 316, and transmitter carrier 318 are formed of recyclable or biodegradable material, and these components may be recycled or composted. Thus, it should be recognized that biosensor inserters 100 of the present disclosure dramatically reduce the amount of medical waste and increase the amount of recyclable or biodegradable material.

Figure 7:
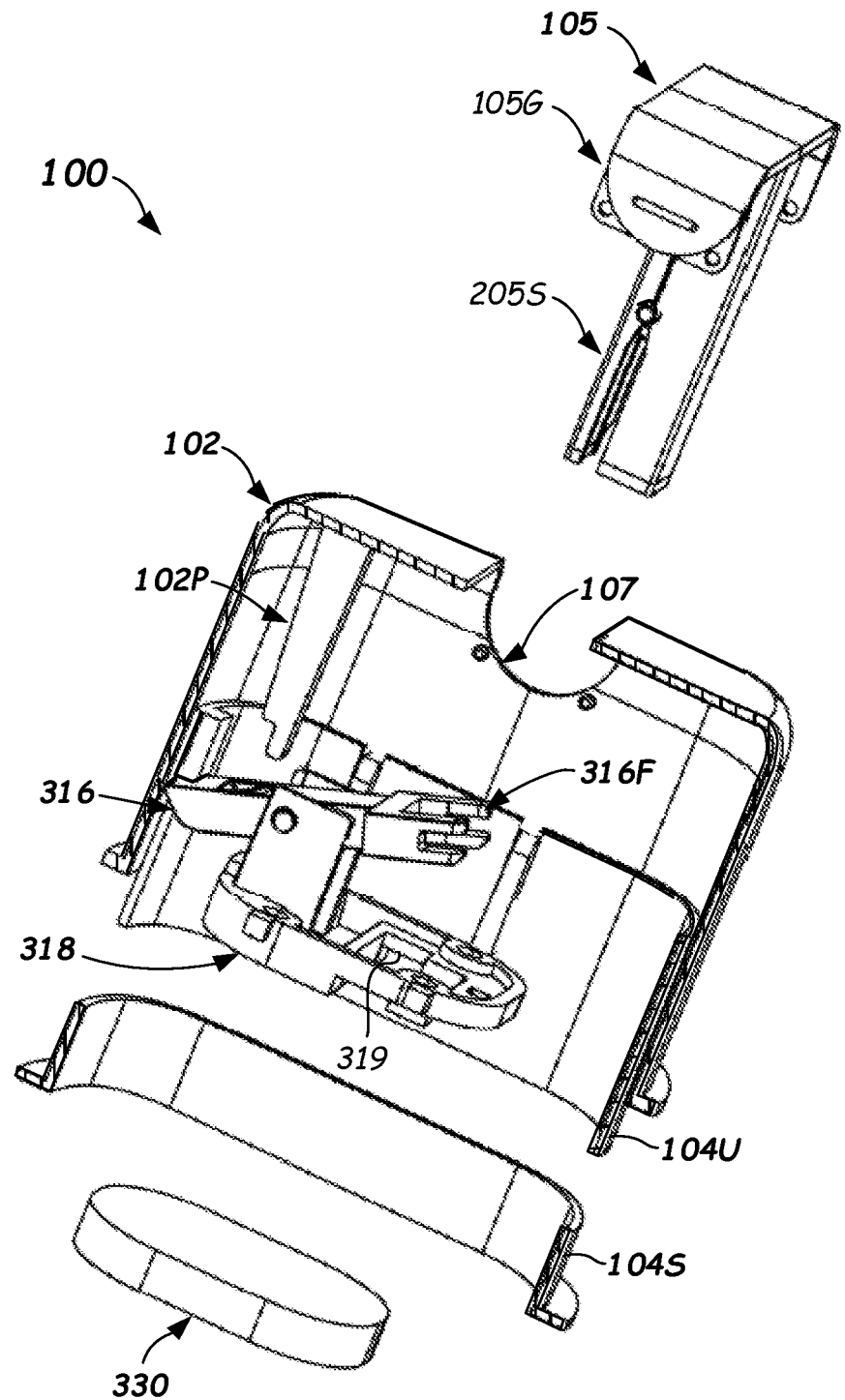
FIG. 7 is a cross-sectioned, exploded side view of a biosensor inserter illustrated with the trocar and trocar holder removed from the remainder of the biosensor inserter in accordance with one or more embodiments provided herein.

FIG. 7 illustrates an exploded view of various components of the biosensor inserter 100.

Referring now to FIG. 8, an embodiment of a method 800 of using a biosensor inserter (e.g., biosensor inserter 100) to insert a biosensor (e.g., biosensor 314) into a user is described. The method 800 comprises, in block 802, providing the biosensor inserter (e.g., biosensor inserter 100) comprising: a push member (e.g., push member 102) including a receiver (e.g., receiver 107), a trocar holder (e.g., trocar holder 105) inserted in the receiver, the trocar holder including a sheath portion (e.g., sheath portion 205S), and a contact member (e.g., contact member 104) translatable relative to the push member, and a trocar assembly (e.g., trocar assembly 212) including a trocar (e.g., trocar 212T).

The method 800 further comprises, in block 804, contacting the contact member (e.g., contact member 104) to skin of the user, and in block 806, pushing on the push member (e.g., push member 102) to cause insertion of the trocar (e.g., trocar 212T) and biosensor (e.g., biosensor 314) into the skin. The pushing (force 108) causes the transmitter carrier (e.g., transmitter carrier 318) to translate relative to the contact member.

Further, the method 800 comprises, in block 808, continuing to push the push member (e.g., push member 102) to retract the trocar assembly (e.g., trocar assembly 212) into the sheath portion (e.g., sheath portion 205S), while leaving the biosensor (e.g., biosensor 314) implanted. Finally, the method 800 comprises, in block 810, removing the trocar holder (e.g., trocar holder 105) and trocar assembly (e.g., trocar assembly 212) from the receiver (e.g., receiver 107). Following removal, the trocar holder 105, and trocar assembly 212 may be discarded as medical waste, along with the skirt 104S, if contaminated with blood. The remainder of the biosensor inserter 100 can be recycled.

The foregoing description discloses only example embodiments. Modifications of the above-disclosed apparatus and methods, which fall within the scope of this disclosure, will be readily apparent to those of ordinary skill in the art.

What is claimed is:

1. A biosensor inserter configured to insert a biosensor, comprising:
    a push member including a receiver;
    a contact member translatable relative to the push member;
    a trocar holder configured to receive a trocar assembly, the trocar assembly including a trocar therein, the trocar holder configured to be insertable into and removable from the receiver;
    a transmitter carrier translatable relative to the contact member, the transmitter carrier configured to support a transmitter and a sensor assembly during insertion of the biosensor; and
    a pivot member configured to pivot on the transmitter carrier, the pivot member including a latch end and a forked end, the forked end including a first fork and a second fork that straddle a sheath portion of the trocar holder.

2. The biosensor inserter of claim 1 wherein the receiver comprises a pocket formed in a top portion of the push member.

3. The biosensor inserter of claim 1 wherein the trocar holder comprises a grasping portion and the sheath portion, wherein the trocar assembly is retractable inside of the sheath portion after insertion of the biosensor.

4. The biosensor inserter of claim 1 wherein the trocar holder containing the trocar assembly are removable from the receiver of the push member.

5. The biosensor inserter of claim 1 wherein the transmitter carrier includes an aperture configured to receive the sheath portion during the insertion of the biosensor.

6. The biosensor inserter of claim 1 wherein the first fork and the second fork each comprise an open-ended groove formed therein and configured to receive a wing of the trocar assembly therein.

7. The biosensor inserter of claim 1 wherein the push member further includes a push element configured to engage with the pivot member.

8. The biosensor inserter of claim 1 wherein the sheath portion comprises slots formed in sides of the sheath portion that are configured to receive wings of the trocar assembly.

9. A biosensor inserter, comprising:
a push member having a push element and a receiver;
a trocar holder including a sheath portion, wherein the trocar holder is received in the receiver;
a contact member configured to telescope relative to the push member;
a transmitter carrier configured to support a transmitter and a sensor assembly during insertion of a biosensor;
a pivot member configured to pivot on the transmitter carrier; and
a trocar assembly supported by the pivot member during insertion and retraction, the trocar assembly receivable in the sheath portion upon retraction,
wherein the sheath portion comprises one or more retention features configured to secure the trocar assembly to the sheath portion,
wherein the one or more retention features comprise a narrowed portion of a slot formed in a side of the sheath portion configured to receive wings of the trocar assembly.

10. The biosensor inserter of claim 9, wherein the contact member and the transmitter carrier are rotationally aligned using one or more alignment features.

11. The biosensor inserter of claim 9, wherein the transmitter and the sensor assembly is configured to adhere to a user.

12. The biosensor inserter of claim 9, wherein at least one of the push member, the contact member, the pivot member, or the transmitter carrier are formed of biodegradable material.

13. The biosensor inserter of claim 9, wherein at least one of the push member, the contact member, the pivot member, or the transmitter carrier are formed of recyclable material.

14. A method of using a biosensor inserter to insert a biosensor into a user, comprising:
providing the biosensor inserter comprising:
a push member having a push element and a receiver,
a trocar holder including a sheath portion, wherein the trocar holder is received in the receiver;
a contact member configured to telescope relative to the push member;
a transmitter carrier configured to support a transmitter and a sensor assembly during insertion of the biosensor;
a pivot member configured to pivot on the transmitter carrier; and
a trocar assembly supported by the pivot member during insertion and retraction, the trocar assembly receivable in the sheath portion upon retraction,
wherein the sheath portion comprises one or more retention features configured to secure the trocar assembly to the sheath portion,
wherein the one or more retention features comprise a narrowed portion of a slot formed in a side of the sheath portion configured to receive wings of the trocar assembly;
contacting the contact member to skin of the user;
pushing on the push member to cause insertion of the trocar assembly and the biosensor into the skin;
continuing to push the push member to retract the trocar assembly into the sheath portion, while leaving the biosensor implanted; and
removing the trocar holder and the trocar assembly from the receiver.

15. The method of claim 14, wherein the pivot member comprises a latch end.

16. The method of claim 14, wherein the pivot member comprises a forked end including a first fork and a second fork that straddle the sheath portion of the trocar holder.

17. The method of claim 16, wherein the first fork and the second fork include an open-ended groove configured to receive the wings of the trocar assembly.

18. The method of claim 14, wherein the transmitter carrier is translatable relative to the contact member.

19. The method of claim 14, wherein the biosensor inserter further comprises a skirt removably fastened to the contact member.

20. The method of claim 19 further comprising:
removing the skirt from the contact member.

* * * * *